United States Patent [19]

Lee et al.

[11] Patent Number: 5,349,847
[45] Date of Patent: Sep. 27, 1994

[54] RELEASABLE STATIONARY PLATE FOR RHEOMETER

[75] Inventors: Chun D. Lee; Donald L. Broughton, both of Cincinnati, Ohio

[73] Assignee: Quantum Chemical Corporation, Cincinnati, Ohio

[21] Appl. No.: 159,082

[22] Filed: Nov. 29, 1993

[51] Int. Cl.$^5$ .............................................. G01N 11/14
[52] U.S. Cl. ...................................... 73/54.28; 73/846
[58] Field of Search .................... 73/54.28, 54.35, 841, 73/843, 846, 847

[56] References Cited

U.S. PATENT DOCUMENTS

| | | | |
|---|---|---|---|
| 3,479,858 | 11/1969 | Umeno et al. | 374/48 |
| 3,488,992 | 1/1970 | Veith et al. | 374/48 |
| 3,681,980 | 8/1972 | Decker | 73/794 |
| 4,095,461 | 6/1978 | Starita | 73/846 |
| 4,343,190 | 8/1982 | Danko et al. | 73/846 |
| 4,501,155 | 2/1985 | Garritano | 73/847 |
| 4,539,838 | 9/1985 | Fraleigh | 73/54.23 |
| 4,552,025 | 11/1985 | Barker et al. | 73/846 |
| 4,667,519 | 5/1987 | Burg et al. | 73/815 |
| 5,079,956 | 1/1992 | Burhin et al. | 73/846 |

Primary Examiner—Hezron E. Williams
Assistant Examiner—Joseph W. Roskos
Attorney, Agent, or Firm—Gerald A. Baracka; William A. Heidrich

[57] ABSTRACT

A stationary plate assembly for a rheometer that selectively provides steady state and dynamic testing of melt viscoelastic characteristics of a material sample. The stationary plate assembly has a stationary sample plate magnetically coupled to its supporting member. Therefore, after the steady state testing is complete, the movable plate, material sample and stationary plate may be moved vertically away from the stationary plate supporting member. Therefore, any spurious, erratic rotations of the movable plate when the rheometer is switched form the steady state test mode to the dynamic test mode will not cause a further working of the material sample.

8 Claims, 2 Drawing Sheets

RELEASABLE STATIONARY PLATE FOR RHEOMETER

BACKGROUND OF THE INVENTION

1. Field of the Invention

The present invention relates generally to a stationary plate rheometer; and more particularly, the invention provides a method and apparatus for measuring the melt viscoelastic properties of a material sample with a rheometer having a releasable stationary sample plate.

2. Description of Related Art

Testing for complete rheological data requires testing both the steady state and dynamic viscoelastic properties of a material sample. The rheological tests are performed to determine the molten viscoelastic properties of the material sample. Using a rheometer a material sample is placed between sample plates designed to contain the material, and the material sample is heated to its molten state.

The steady state viscoelastic properties are a measure of the material's shear properties, that is, the working properties of the material that will arise, for example, when molding material in a molten state. The dynamic viscoelastic properties are a measure of the intrinsic of properties of the material. To determine the steady state viscoelastic properties, one of the plates is held stationary; and the other plate is driven through a continuous rotation. The steady state viscoelastic properties are determined by measuring the resistance to rotation of the driven plate. The dynamic viscoelastic properties are determined in a similar manner in which a material sample is located between a stationary plate and a moveable plate. However, in this case, the moveable plate oscillates through a predetermined arc, and the dynamic viscoelastic properties are determined by measuring the resistance to rotation of the oscillating plate. Both the steady state test and the dynamic test may be performed on a single rheometer such as that disclosed in U.S. Pat. No. 4,539,838 issued to M. F. Fraleigh on Sep. 10, 1985.

Many commercially available cone and plate or parallel plate rheometers contain rotary drives which are switchable between a continuous rotation and an arcuate oscillation have a particular disadvantage, That being, when switching between the continuous rotation mode and the oscillation mode, the output shaft of the rotary drive mechanism experiences a rapid, erratic rotation that jerks or wrenches the driven moveable plate through an unanticipated incremental angular displacement or arc, of 60° to 90° relative to the stationary plate. At the end of the steady state test, the material sample may be worked such that it is highly viscous and presents a high resistance connection between the moveable and stationary plates. Therefore, the unanticipated rotation wrenching the moveable plate relative to the stationary plate when the rheometer is drive is changed from the continuous rotation to the arcuate oscillation may potentially damage the sample plates or the rheometer machine structure itself.

In addition, the unanticipated jerking or wrenching action provides an unanticipated working of the material sample which changes the rheological data, that is, the rheological characteristics of the material sample. Further, the magnitude of the change in rheological data is not known and unpredictable. Consequently, the rheological base line for subsequent testing of dynamic characteristics of the material sample are thus changed; and the rheological data obtained during the dynamic testing is skewed. Therefore, for the most accurate results, the material sample sheared in the steady state test should not be used for the dynamic test.

SUMMARY OF THE INVENTION

To overcome the disadvantages of the above-described mechanisms, the present invention provides a stationary plate that is releasably coupled to the rheometer. The present invention permits the moveable plate, the material sample and the stationary plate to be disconnected from the rheometer frame during the time the rheometer rotary drive is switched between the continuous rotation and arcuate oscillation modes of operation. Therefore, the invention is particularly useful with those rheometers experiencing an unanticipated rotation or wrenching of the moveable plate when switching between the continuous rotation and arcuate oscillation modes of operation. The invention is especially well-suited for use in rheological testing in which both the dynamic intrinsic properties and the steady state shear properties of a single material sample are to be determined.

According to the principles of the present invention and in accordance with the described embodiments, a stationary sample plate assembly for a rheometer includes a stationary plate releasably coupled to its support member by means of a magnet such that the moveable plate, material sample and the stationary plate may be separated as a unit from the support member for the stationary plate. The above construction has the advantage that when switching between the continuous rotation and arcuate oscillation drive modes, the unanticipated wrenching or twisting of the moveable plate may occur without damage to the rheometer and without degrading the integrity of the material sample. Since the material sample which was sheared in the steady state test does not experience any further working, the same material sample may be used for the dynamic testing. Further, the magnetic releasable coupling of the stationary member permits easy removal of the stationary plate which, for example, facilitates cleaning the stationary plate. A further advantage of the stationary plate assembly is that its construction permits it to be easily retrofitted and applied to rheometers in the field.

These and other objects and advantages of the present invention will become more readily apparent during the following detailed description in conjunction with the drawings herein.

DETAILED DESCRIPTION OF THE INVENTION

Figure 1:
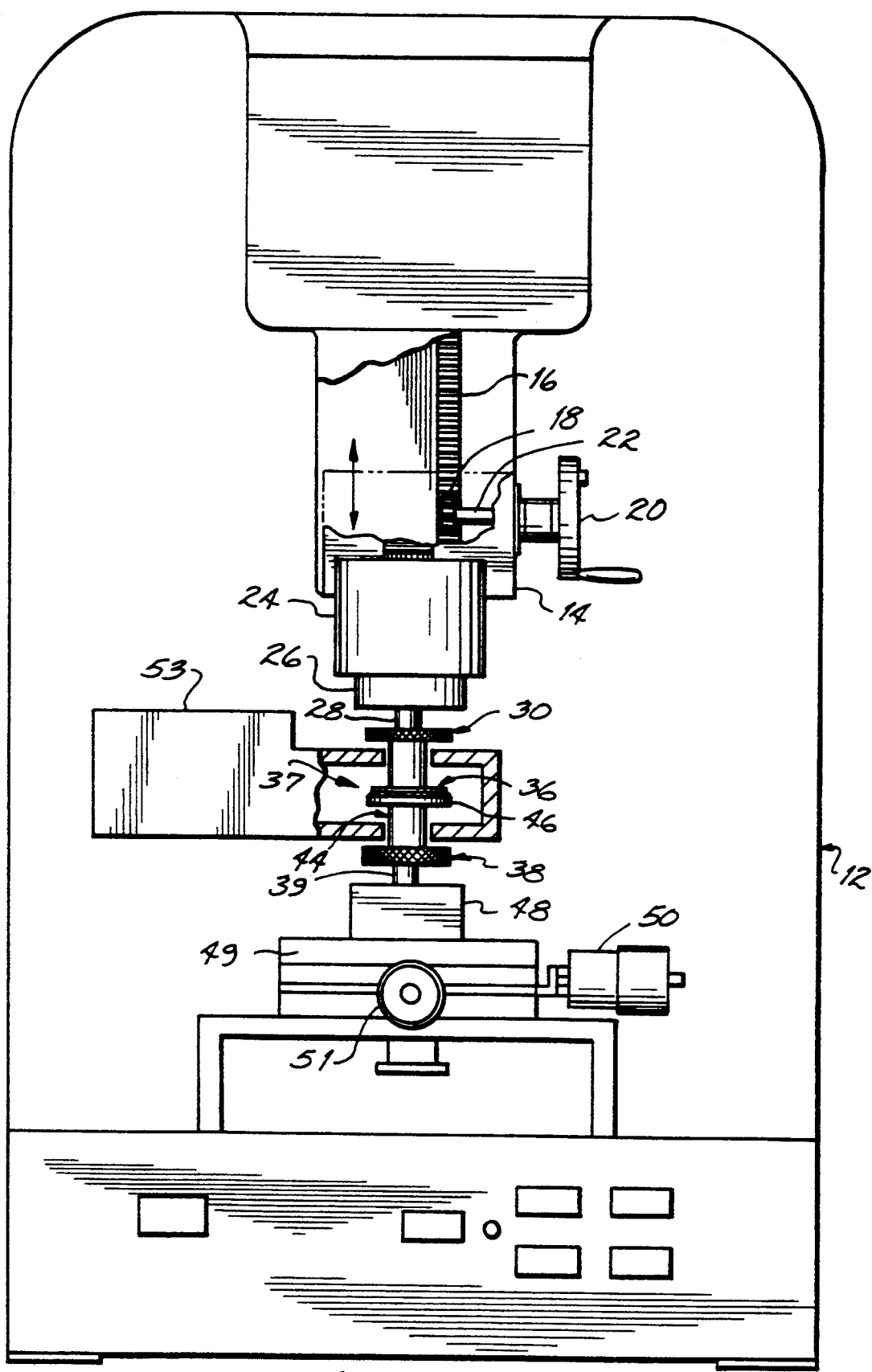
FIG. 1 is a schematic front elevation of a parallel plate rheometer.

FIG. 1 is a schematic illustration of a parallel plate rheometer 10. The rheometer includes a frame 12 having a slide 14 mounted for vertical motion on the frame 12. The vertical translation of the slide 14 may be accomplished using several known means such as, for example, a toothed rack 16 mounted to the frame 12 which receives gear teeth of a pinion 18 rotatably mounted within the slide 14. The pinion 18 is connected to a handwheel 20 by means of a shaft 22. Therefore, an operator rotating the handwheel 20 also rotates shaft 22 and pinion 18 which causes the slide 14 to move vertically up and down with respect to the rack 18 and frame 12. The motion of the slide 14 may also be guided by linear bearing surfaces, such as ways, (not shown).

Typically an electric motor 24 is mounted on the slide 14. The motor 24 is coupled through a rotary drive 26 to an output drive shaft 28. The rotation of the output drive shaft may be switched to select either a continuous rotation, or an arcuate oscillation. Those two selectable drive modes may be achieved by engaging drive mechanisms within the rotary drive 26 or by electrical control of the motor 24. In either event, it has been observed that the output drive shaft 28 experiences an erratic, rotational motion when switching between the continuous rotation and the arcuate oscillation.

Figure 2:
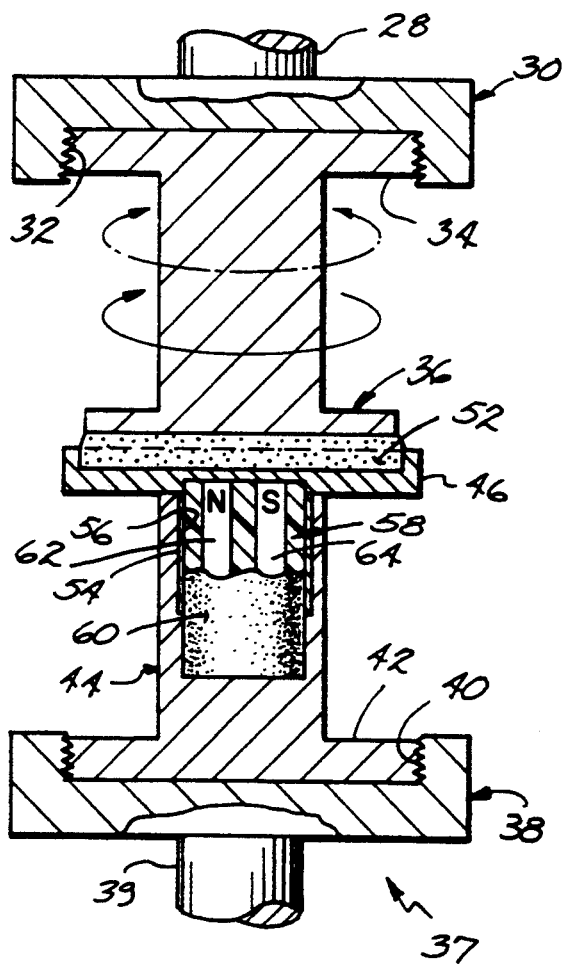
FIG. 2 is a cross-sectional view of the sample plate assembly illustrating the stationary plate assembly of the present invention.

A first nut 30 is rotatably mounted on the end of drive shaft 28. As shown in FIG. 2, the nut 30 has an internal threaded bore 32 that receives a threaded end 34 of a moveable sample plate 36 forming part of a sample plate assembly 37. A second nut 38 is rotatably mounted on the end of a mounting member 39 has an internal threaded bore 40 that receives a threaded end 42 of a support member 44. As shown in FIG. 1, the mounting member 39 holding the second nut 38 is operably coupled to a torque transducer 48 which, in turn, is supported on a table 49 having positioning mechanisms 50 and 51. The positioning mechanisms 50, 51 are operative to translate the table 49 along perpendicular axes of motion thereby permitting a stationary sample plate 46 to be precisely aligned with the moveable sample plate 36.

In use, the handwheel 20 is used to move the first nut 30 vertically upward away from the second nut 38. The moveable plate 36 is threadedly connected with the first nut 30, and the sample plate structure including the stationary plate 46 and support member 44 are threadedly engaged with the second nut 38. Thereafter, the handwheel 20 is used to move the movable plate 36 vertically downward to bring the sample plates 36, 46 into close proximity; and the positioning mechanisms 50, 51 are used to coaxially align the centerline of the moveable plate 36 and stationary plate 46. The handwheel 20 is then used to move the moveable sample plate 36 vertically upward and away from the stationary plate 46. A material sample 52 is placed on the stationary sample plate 46, and the handwheel 20 is used to move the moveable plate 36 vertically downward into contact with the material sample 52. Power is applied to heaters 53 (FIG. 1) which are effective to melt the material sample 52 between the sample plates 36, 46. The handwheel 20 is further used to move the movable plate 36 to a working position with respect to the stationary plate 46. The working position provides a predetermined gap between opposing surfaces of the sample plates 36, 46. The movable plate 36 is sufficiently smaller than the stationary plate 46 so that there is a minimal clearance between edges of the sample plates which will allow the moveable plate 36 to rotate with respect to but without being in contact with the stationary plate 46. In moving to the working position, the moveable plate may squeeze some of the molten material sample out from between the sample plates; and that excess material will have to be trimmed off prior to initiating the viscosity tests.

Controls and/or mechanisms on the motor 24 and rotary drive 26 are switched to provide the output shaft 28 and movable plate 36 with a continuous rotation with respect to the stationary plate 46. The resistance to rotation is measured with the transducer 48 thereby providing rheological data associated with the steady state properties of the material sample, that is, the material shear characteristics. If at the end of the steady state test, the output drive shaft 28 is switched to select the arcuate oscillation, it has been observed that the moveable plate 36 will experience an unpredictable, erratic, incremental rotation with respect to the stationary plate 46.

With known sample plate structures, the support member 44 is rigidly connected to and is an inseparable unitary piece with the stationary sample plate 46. Therefore, the erratic rotation of the output drive shaft 28 when the drive is switched to the arcuate oscillation continues to work the material sample and changes the rheological data, that is, the rheological characteristics of the material sample after the end of the steady state test, but before the beginning of the dynamic test. Further, the change in rheological data is not known, and it changes the rheological base line of the testing of dynamic characteristics to follow. Knowing that the integrity of the material sample has been degraded by the erratic working of the material sample, the movable and stationary plates must then be separated; the old material sample replaced with a new material sample which is used for the dynamic tests.

Figure 3:
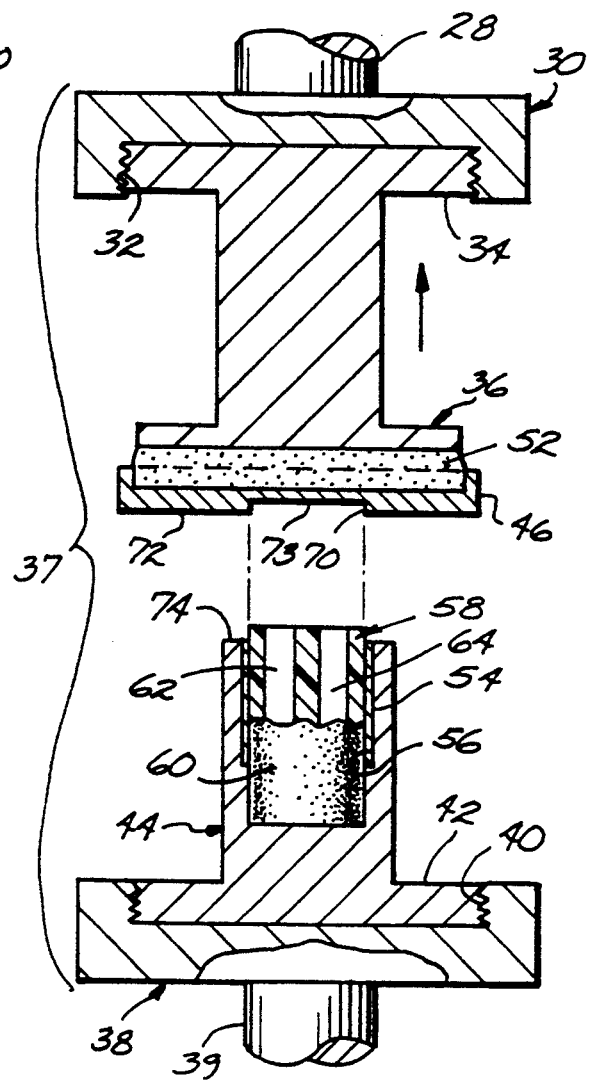
FIG. 3 is a cross-sectional view illustrating the separation of the sample plate from the support member in response to a vertical translation of the sample plate assembly.
Figure 4:
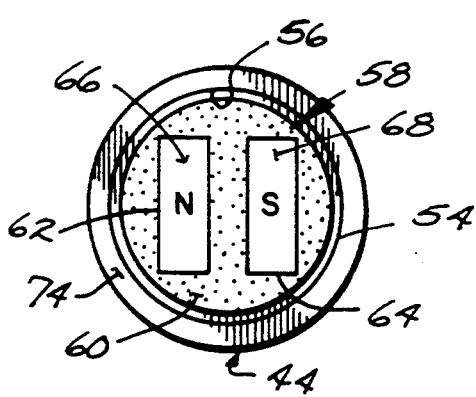
FIG. 4 is a top view of the support member illustrating the magnetic coupling of the present invention.

To overcome the above problem, as shown in FIGS. 2-4, the present invention provides a stationary plate assembly in which the stationary plate 46 is a separate piece and not rigidly connected to the support member 44, The stationary plate 46 is made with a material that is ferromagnetic or otherwise attracted by magnetic force, The support member 44 has a sleeve 54 inserted therein. Within the internal bore 56 of sleeve 54 is a magnet 58 supported within the bore 56 by epoxy 60. The magnet 58 is comprised of two magnetic rods 62, 64 having opposing magnetic poles 66, 68, for example, a north pole and a south pole, respectively, located at one end of the support member 44.

The stationary plate 46 has a centrally located counterbore 70 on its outside surface 72. The assembly of the epoxy 60 and the magnetic rods 60 and 64 extends beyond one end 74 of the support member 44 a distance approximately equal to the depth that the counterbore 70 extends into the surface 72 of the stationary plate 46. Therefore, the ends of the magnetic rods 62 and 64 contact the inside flat surface 73 in the counterbore 70 of the stationary sample plate 46 to form a magnetic coupling that secures the stationary plate 46 to the support member 44. The magnetic coupling is such that the stationary sample plate 46 does not experience rotation with respect to the support member 44 while the moveable plate 36 is rotating.

Referring to FIG. 3, in use, at the completion of the steady state test, the material sample 52 between the sample plates 36, 46 has a high viscosity which provides a relatively tight and high resistance connection between the moveable plate 36 and stationary plate 46, Therefore, with the stationary plate assembly of the present invention, the operator may use the handwheel 20 to translate a unitary assembly of the moveable plate 36, material sample 52 and stationary plate 46 in the vertically upward direction. The upward motion of the moveable plate 36, material sample 52 and stationary plate 46 breaks the magnetic coupling between the stationary plate 46 and the support member 44 and separates the stationary sample plate 46 from its support member 44.

Thereafter, controls and or mechanisms on the motor 24 and rotary drive 26 are switched to select the arcuate oscillation of the output drive shaft 28. If during the selection of the arcuate oscillation, the output drive shaft 28 experiences an erratic, unpredictable rotation, the output drive shaft 28, moveable member 36, material sample 52 and stationary plate 46 rotate as a unitary assembly with respect to the frame 12. Consequently, the material sample is not worked, and the rheological data is not changed. After the arcuate oscillation has been selected, the handwheel 20 is used to bring the stationary plate back into contact with the support member 44 thereby reengaging the magnetic coupling. Thereafter, the drive shaft 28 and moveable plate 36 are moved through the arcuate oscillations with respect to the stationary plate 46 as required to collect rheological data associated with the dynamic viscoelastic characteristics of the material sample.

Using the stationary plate assembly having the magnetic coupling of the present invention, the same material sample may be used to successively perform the steady state test and the dynamic test to collect accurate rheological data in association with each test.

While the present invention has been set forth by a description of the embodiment in considerable detail, it is not intended to restrict or in any way limit the claims to such detail. Additional advantages and modifications will readily appear to those who are skilled in the art. For example, in the described embodiment, the moveable plate is located vertically above the stationary plate. Alternatively, with a different rheometer which inverts the location of the rotary drive, the present invention may be utilized with the moveable plate located vertically below the stationary plate. Further, the invention has been described with the magnetic coupling connecting the stationary plate to its support member. Alternatively, the moveable plate may be a separate piece from its support member, and the magnetic coupling used to connect the moveable plate to its mounting member. The counterbore within the stationary plate into which the coupling magnet is inserted is described as being cylindrical in shape. To provide a more secure coupling that further inhibits the stationary plate from rotating with respect to its support member, the counterbore and associated end of the coupling magnet may have a non-cylindrical geometric shape, such as, for example, a square shape. Further, the releasable coupling between the stationary plate 46 and its support member 44 may be provided by permanent or electric magnets. The invention in its broadest aspect is therefore not limited to the specific detail shown and described. Accordingly departures may be made from such details without departing from the spirit and scope of the invention.

What is claimed is:

1. A stationary plate assembly for a rheometer used for testing the melt viscoelastic properties of a material sample, the rheometer having a frame supporting a rotary drive having a drive shaft selectively switchable between a continuous rotation and an arcuate oscillation, the drive shaft being coupled to a movable plate, the rheometer further including a positioning mechanism for moving the movable plate relative to the stationary plate assembly, the stationary plate assembly comprising:

a support member adapted to be coupled to the frame in an aligned relationship to the movable plate;
   a sample plate for supporting the material sample with respect to the movable plate; and
   means for releasably coupling the sample plate to the support member to permit the positioning mechanism to separate the movable plate, the material sample and the sample plate as a unit from the support member, thereby allowing the movable plate, the material sample and the sample plate to rotate as a unit with respect to the support member as may occur when selectively switching the drive shaft between the continuous rotation and the arcuate oscillation.

2. The stationary plate assembly of claim 1 wherein the means for releasably coupling the sample plate includes a magnet located in one of the sample plate and the support member.

3. The stationary plate assembly of claim 2 wherein the sample plate is made with a material attracted by a magnet and the means for releasably coupling the sample plate further includes a magnet located in the support member.

4. The stationary plate assembly of claim 3 wherein the magnet further includes two magnetic elements having opposite magnetic poles mounted in one end of the support member to magnetically couple the sample plate to the support member.

5. The stationary plate assembly of claim 4 wherein the two magnetic elements are secured in the support member to expose at the one end of the support member ends of the magnetic elements having opposite magnetic poles such that the ends of the magnets contact and magnetically couple the sample plate to the support plate.

6. A sample plate assembly for a rheometer of the type used for testing the melt viscoelastic properties of a material sample, the rheometer having a rotary drive with a drive shaft selectively switchable between a continuous rotation and an arcuate oscillation, the sample plate assembly comprising:

a movable plate adapted to be coupled to the drive shaft;
   a stationary plate assembly adapted to be coupled to the frame in juxtaposition with the movable plate such that the material sample is contained between the movable plate and stationary plate assembly, the stationary plate assembly having
   a support member coupled to the frame,
   a sample plate, and
   means for releasably coupling the sample plate to the support member, whereby the movable plate, the sample material and the sample plate may be separated as a unit from the support member, thereby allowing the movable plate, the sample material and the sample plate to rotate with respect to the support member as may occur when selectively switching the drive shaft between the continuous rotation and the arcuate oscillation.

7. A rheometer of the type used for testing the melt viscoelastic properties of a material sample comprising:
   a frame;

a rotary drive mounted on the frame, the rotary drive having a drive shaft selectively switchable between a continuous rotation and an arcuate oscillation; and a sample plate assembly including a movable plate coupled to the drive shaft, and a stationary plate assembly coupled to the frame in juxtaposition with the movable plate such that the material sample is contained between the movable plate and stationary plate assembly, the stationary plate assembly having a support member coupled to the frame, a sample plate, and means for releasably coupling the sample plate to the support member, whereby the movable plate, the sample material and the sample plate may be separated as a unit from the support member, thereby allowing the movable plate, the sample material and the sample plate to rotate with respect to the support member as may occur when selectively switching the drive shaft between the continuous rotation and the arcuate oscillation.

8. A method of testing the molten viscoelastic properties of a material sample with a rheometer, the material sample being located between a rotatable plate coupled to a drive shaft and a stationary plate coupled to a support member on a frame of the rheometer and held immovable with respect to the rotatable plate, the drive shaft being connected to a rotary drive mounted on the frame, the rotary drive being switchable to selectively move the drive shaft in first, a continuous rotation and second, an arcuate oscillation, the method comprising:

switching the rotary drive to select the continuous rotation of the drive shaft;

moving the drive shaft and the rotatable plate in the continuous rotation;

stopping the continuous rotation of the drive shaft and rotatable plate;

moving the stationary plate relative to the support member on the frame to separate the stationary plate from the support member to create a unitary assembly of the rotatable plate, the material sample and the stationary plate coupled to the drive shaft and movable as a unit with respect to the frame;

switching the rotary drive to select the arcuate oscillation of the drive shaft;

moving the stationary plate relative to the support member on the frame to join the stationary plate to the support member; and moving the drive shaft and the rotatable plate in the arcuate oscillation.

* * * * *